United States Patent [19]
Anderson

[11] Patent Number: 5,325,746
[45] Date of Patent: * Jul. 5, 1994

[54] WIRE GUIDE CONTROL HANDLE

[75] Inventor: Burton A. Anderson, Bloomington, Ind.

[73] Assignee: Cook Incorporated, Bloomington, Ind.

[*] Notice: The portion of the term of this patent subsequent to Nov. 3, 2009 has been disclaimed.

[21] Appl. No.: 938,885

[22] Filed: Aug. 31, 1992

Related U.S. Application Data

[63] Continuation-in-part of Ser. No. 767,273, Sep. 27, 1991, Pat. No. 5,159,861.

[51] Int. Cl.⁵ .................... A61B 17/00; B65H 20/00
[52] U.S. Cl. ........................... 81/487; 24/115 M; 24/136 R; 604/159; 606/1; 128/772; 128/657
[58] Field of Search .............. 81/487; 606/1; 128/772, 128/657; 24/115 R, 115 F, 115 G, 115 M, 136 R; 226/158, 127, 162; 254/134.5 R, 134.3 F; 604/159, 170

[56] References Cited

U.S. PATENT DOCUMENTS

| | | |
|---|---|---|
| 1,442,862 | 1/1923 | Curtis . |
| 2,220,203 | 11/1940 | Branin ................. 24/136 R |
| 3,312,128 | 4/1967 | Wasson ................. 81/487 |
| 4,619,274 | 10/1986 | Morrison ................. 128/772 |
| 4,858,810 | 8/1989 | Intlekofer et al. ................. 226/127 |
| 4,860,742 | 8/1989 | Park et al. ................. 128/303 |
| 4,907,332 | 3/1990 | Christain et al. ................. 29/237 |
| 5,137,517 | 8/1992 | Loney et al. ................. 24/115 M |

FOREIGN PATENT DOCUMENTS

| | | |
|---|---|---|
| 0328760 | 8/1989 | European Pat. Off. . |
| 0397995 | 7/1924 | Fed. Rep. of Germany ... 24/115 M |
| 397995 | 7/1924 | Fed. Rep. of Germany . |
| 507177 | 8/1930 | Fed. Rep. of Germany . |
| 9004994 | 5/1990 | PCT Int'l Appl. . |

OTHER PUBLICATIONS

European Search Report for counterpart EPC application, dated Jan. 6, 1993, indicating the relevancy attached to the above-listed references by the European Examiner.

Primary Examiner—Roscoe V. Parker
Attorney, Agent, or Firm—Richard J. Godlewski

[57] ABSTRACT

A lockable wire guide control handle for grasping and manipulating a wire guide. The control handle includes an elongated member and a thumb slide positioned in a retention channel formed in the distal portion of the elongated member. The proximal portion of the elongated member is cylindrical having an enclosed passageway extending longitudinally therethrough, which is offset for passage of the wire guide therethrough. The distal portion of the elongated member includes a dovetail-shaped retention channel, the bottom surface including an inclined slot for positioning the wire guide therein. The thumb slide includes a mating dovetail-shaped tenon positioned in the retention channel. Extending from the flat surface of the dovetail-shaped tenon is an inclined projection for fixedly positioning the wire guide in the inclined slot. The inclined slot and projection have a variable, uniform spacing therebetween for fixedly positioning various diameter wire guides therein.

19 Claims, 5 Drawing Sheets

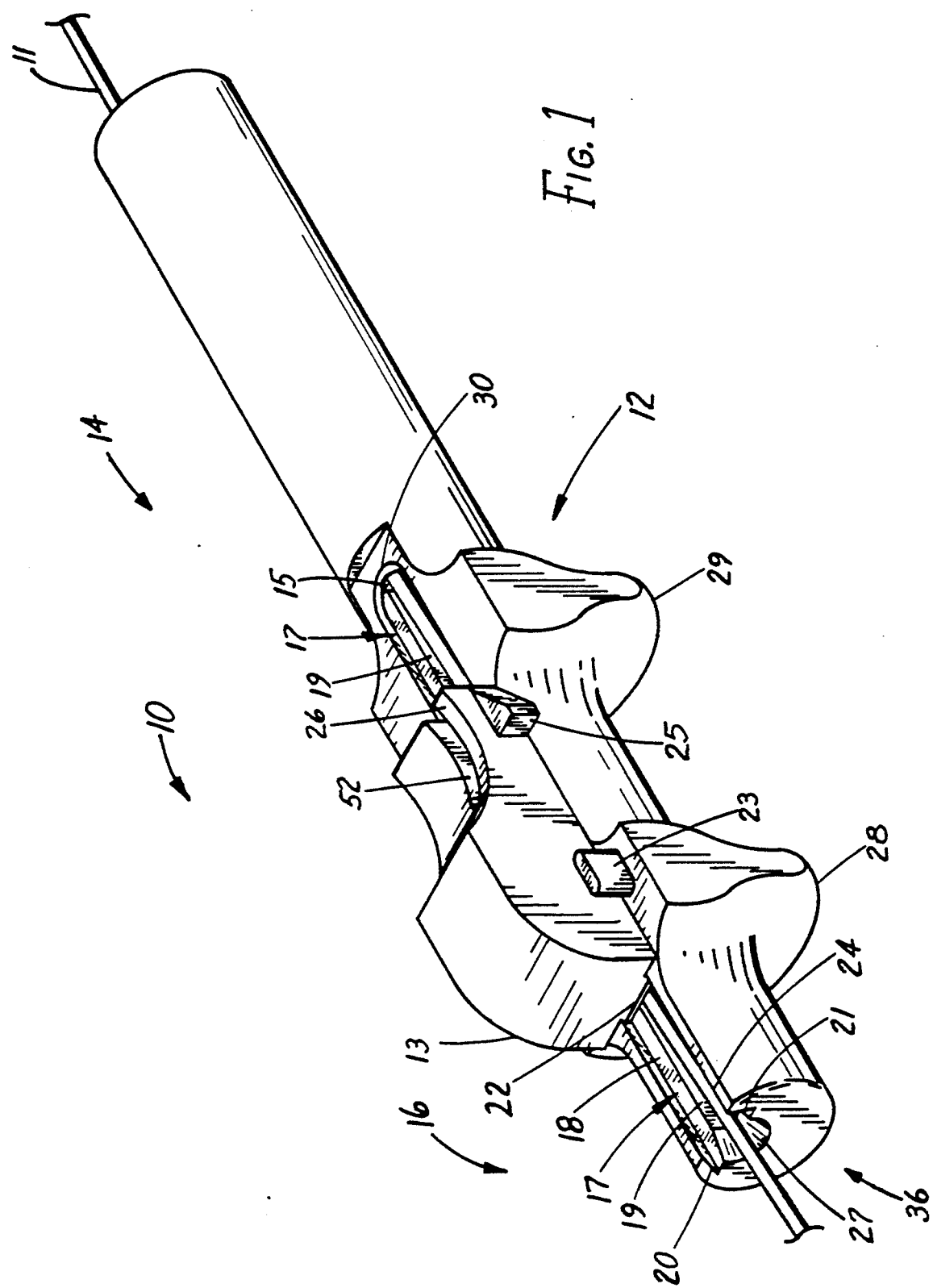

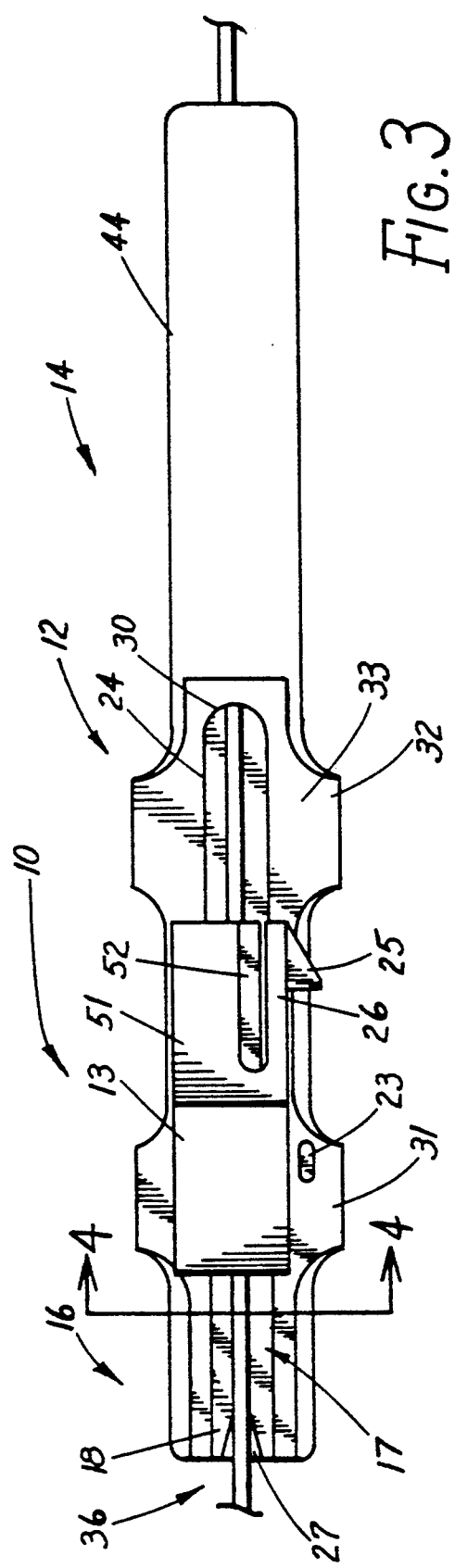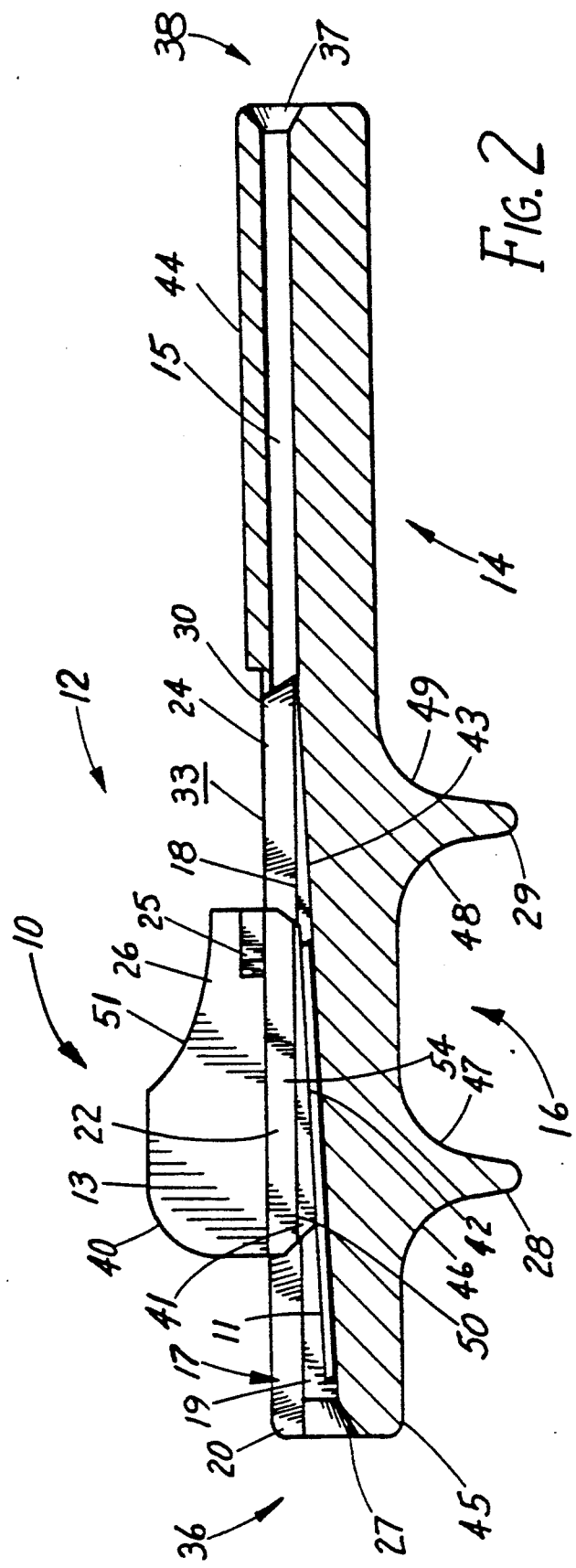

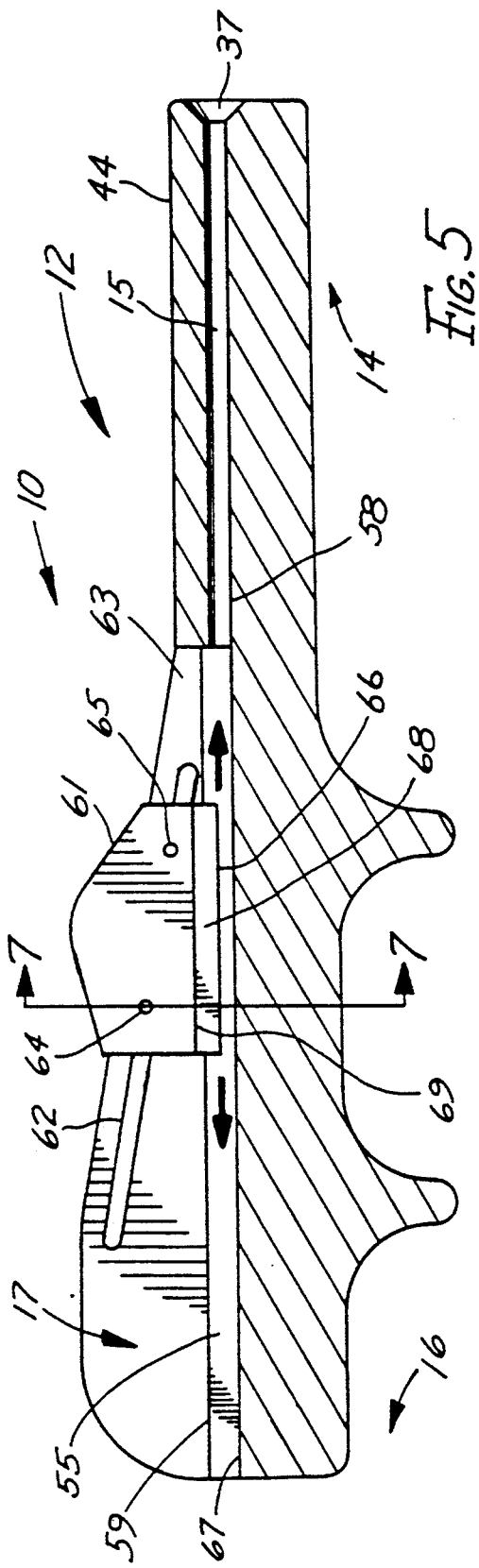
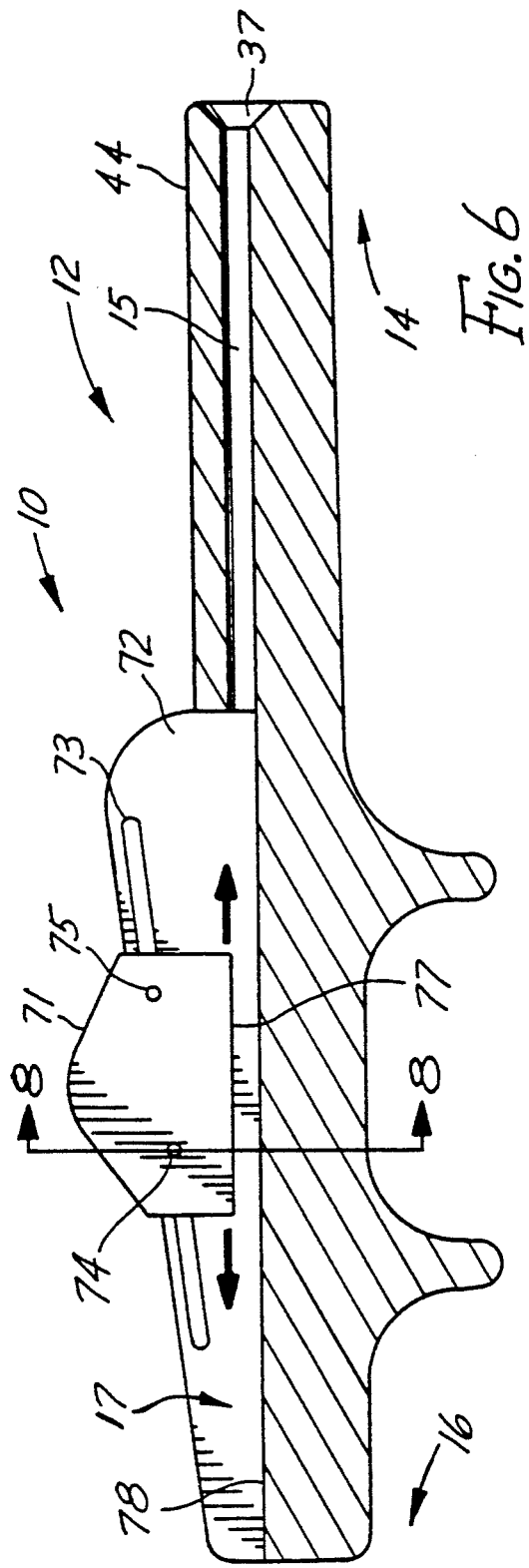

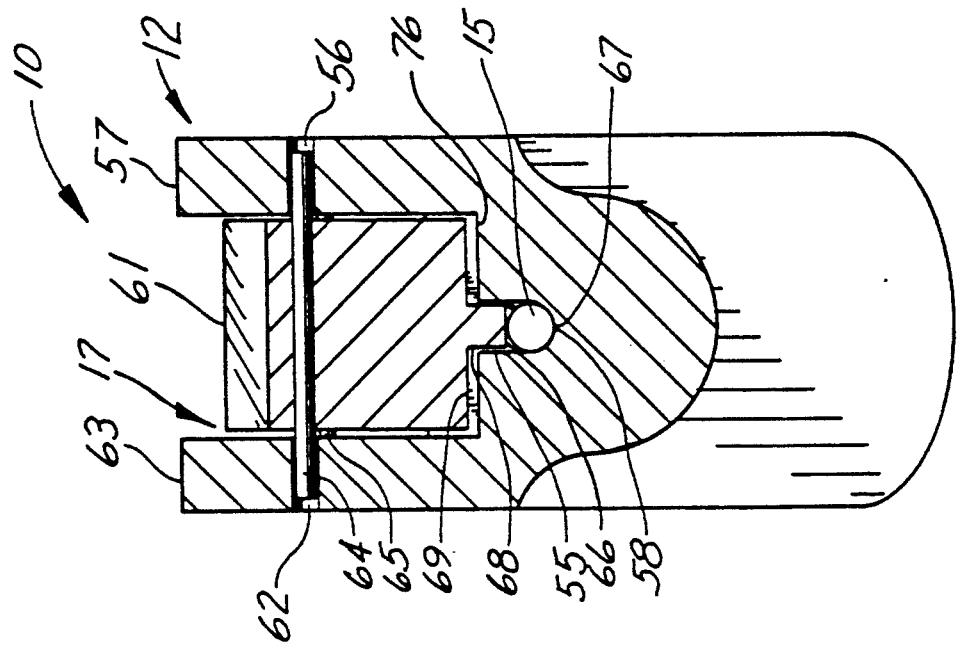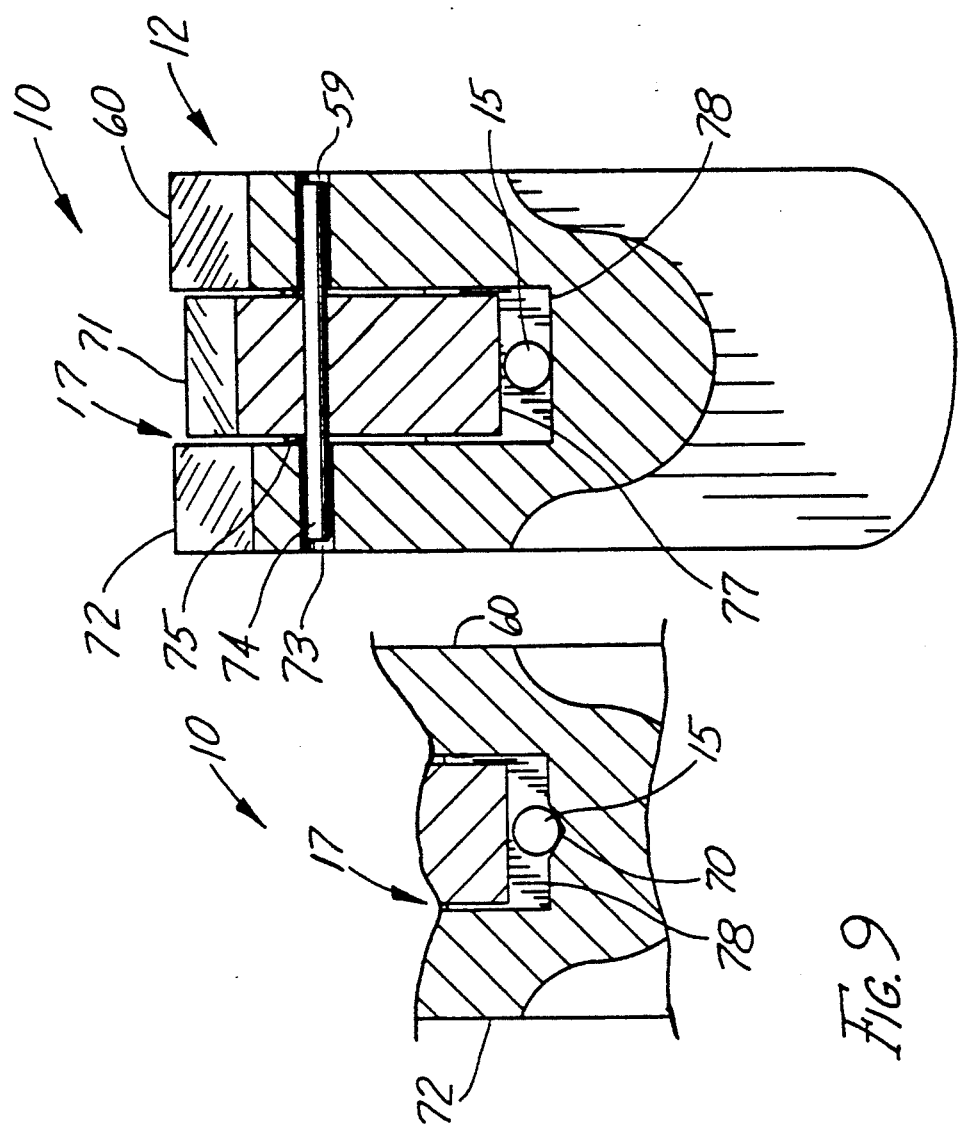

WIRE GUIDE CONTROL HANDLE

CROSS-REFERENCE TO RELATED APPLICATIONS

This application is a continuation-in-part of U.S. application Ser. No. 07/767,273, filed Sep. 27, 1991, and now U.S. Pat. No. 5,159,861 and entitled "Wire Guide Control Handle."

TECHNICAL FIELD

This invention relates generally to medical instruments for grasping and manipulating wire guides and, in particular, to a wire guide control handle having a slidable piece for locking wire guides of various diameters therein.

BACKGROUND OF THE INVENTION

Wire guide handles and pin vises are used for grasping and manipulating wire guides during medical procedures commonly involving percutaneous access to the vascular system in which the wire guide is advanced and rotated through tortuous vessels. One side mount wire guide gripping device includes a cylindrical body and a slot extending longitudinally for the entire length of the device for side loading a wire guide therein. The device further includes two biased closed jaws on either side of the slot and two compression handles for opening the jaws. A problem with this device is that when rotating the device for torquing the wire guide, one of the compression handles may be pressed inadvertently. As a result, the jaws are separated and the wire guide released. Another problem with this device is that the slot extends the entire length of the device. During use, the smooth, cylindrical proximal end of the wire guide may slide out from between the jaws, thereby exiting the slot and device.

Another wire guide grasping device is a pin vise having a handle and a slider piece including a slider block, a spring, and a thumb piece. The handle also has a stop for preventing the forward removal of the slider piece. The spring cocks the thumb piece in the slot for preventing inadvertent removal of the slider piece from the rear of the handle. The spring-loaded thumb piece may be momentarily depressed to grip the wire guide in the slot without advancing the slider piece to a locked position. Although suited for its intended purpose, the pin vise includes two pieces that are easily separated, which makes it difficult for a gloved surgeon to reassemble. The pieces are intended to be separated for side loading of a wire guide; however, the rejoining of the interlocking pieces is cumbersome. Furthermore, the pin vise includes a groove at the bottom of a T-slot which inclines upward at the forward end of the vise for wedging a wire guide therein. A thumb piece slides in the T-slot to wedge the wire guide in the upwardly inclined groove. A problem with this arrangement is that the forward moving thumb piece may kink the wire guide in the upwardly inclined groove at the beginning of the incline.

SUMMARY OF THE INVENTION

The foregoing problems are solved and a technical advance is achieved in an illustrative wire guide control handle comprising an elongated member having an enclosed passageway extending longitudinally through a proximal portion for passing a wire guide therethrough. The distal portion of the elongated member includes a retention channel extending longitudinally therethrough and communicating with the enclosed passageway. The retention channel includes a bottom surface having an inclined slot, which extends longitudinally therein and is angled outwardly away from the enclosed passageway for positioning the wire guide therein. The handle also includes a thumb slide having a tenon that is positioned and slidable in the retention channel for fixedly positioning the wire guide in the inclined slot. The thumb slide includes an inclined projection which extends into the inclined slot for fixedly positioning the wire guide in the slot without kinking the guide. The inclined projection and slot have a variable, substantially uniform spacing therebetween for accepting various diameter wire guides as well as for maximizing the contact surface area for fixedly positioning the guide.

The distal portion of the handle further includes a stop extending therefrom about the opening of the retention channel. The slide of the handle includes a catch extending therefrom for engaging the stop when the thumb slide is moved to a forward position for the ready, front-end insertion of the wire guide into the inclined slot and through the enclosed passageway. The retention channel is partially closed at the proximal end for preventing proximal removal of the thumb slide. As a result, the thumb slide is advantageously maintained in the retention channel without concern for separated pieces. When the wire guide is inserted into the inclined slot of the retention channel, the thumb slide is pulled toward the partially closed end of the channel to grasp and fixedly position the wire guide in the inclined slot. The variable, substantially uniform spacing between the projection of the thumb slide and inclined slot advantageously allows the insertion of various diameter wire guides therein without kinking the inserted wire guide.

The retention channel also advantageously includes a dovetail-shaped mortise for receiving a dovetail-shaped tenon extending from the thumb slide. This dovetailed configuration prevents removal of the thumb slide from the channel and also provides for increased compression for grasping and fixedly positioning the wire guide between the inclined slot and thumb slide projection. This added compression fixedly positions the wire guide in the channel both longitudinally and rotationally so that the control handle can readily rotate or torque the wire guide through the tortuous vessels of the vascular system. The cylindrical configuration of the enclosed proximal portion of the control handle also advantageously allows the physician to rotate and torque the handle and wire guide.

A pair of finger retention projections extend radially from the distal portion of the handle and are positioned longitudinally apart opposite the opening of the channel for easy operation of the thumb slide by the physician. The finger retention projections also provide for controlled longitudinal movement of the handle of the fixedly positioned wire guide. The distal end of the retention channel as well as the proximal end of the enclosed passageways are internally tapered for easy insertion of a wire guide into either end of the control handle. Furthermore, the enclosed passageway is offset from the center longitudinal axis of the proximal portion as well as the inclined slot for easy and controlled rotation of the fixedly positioned wire guide when positioned in the vessel of a patient's vascular system. The offset position of the enclosed passageway with respect to the inclined slot also advantageously minimizes the possibility of kinking a fixedly positioned wire guide.

In another embodiment of the present invention, the wire guide control handle comprises an elongated member having a passageway extending longitudinally therein for receiving a wire guide. The passageway includes a support surface for supporting the wire guide. The handle also comprises a slide positioned and slidable in the passageway. The slide has a bottom surface for engaging and fixedly positioning the wire guide in the passageway. The slide also has a plurality of positions in the passageway and is slidable in the passageway such that the bottom surface of the slide and the support surface of the passageway are substantially parallel to one another and variably spaced from one another at all of the positions of the slide in the passageway.

In addition, the support surface of the passageway includes a slot therein and extending longitudinally therethrough. The slide advantageously includes a projection extending therefrom and into the slot. The slot and projection each have a surface such that the surface of the slot and the surface of the slide are substantially parallel to one another and variably spaced from one another at all positions of the slide in the passageway.

The passageway of the control handle has a lateral surface with a slot therein inclined to the bottom surface of the passageway for advantageously varying the space between the bottom surface of the slide and the support surface of the passageway while these surfaces remain substantially parallel to one another at all positions of the slide in the passageway.

The elongated member of the control handle further includes a channel communicating with the passageway. The channel also includes a support surface for supporting the wire guide. In such embodiment, the slide is positioned and slidable in the channel such that the bottom surface of the slide and the support surface of the channel are substantially parallel to one another and variably spaced from one another at all positions of the slide in the channel. The slide has a plurality of positions in the channel and is slidable in the channel.

In still another embodiment of the present invention, the passageway simply includes a V-shaped slot to prevent lateral movement of the wire guide therein.

In another characterization of the present invention, a wire guide control handle comprises an elongated member having a passageway for the support and passage therethrough of a wire guide and wire guide channel means in communication with the passageway and also serving to support the wire guide therein. The handle also comprises a slidable member having a surface thereof slidably moveable in a channel of the channel means and serving to engage with or disengage from the wire guide when in the channel in order to lock or release the guide in the channel means. The handle also includes means for causing the slidable member to slide along an axis inclined to a wire guide support surface of the channel means. The handle is characterized in that the slidable member surface extends only over one planar wire guide support surface and is substantially parallel to the wire guide support surface during all of the movement of the slidable member. The handle is further characterized in that the bottom surface of the channel inclines relative to the longitudinal axis of the elongated member, in that the axis of the slidable member is parallel to the longitudinal axis of the slidable member, and in that the slidable member's surface is inclined at substantially the same angle of inclination relative to the longitudinal axis as the bottom surface.

The handle is further characterized in that a slot is formed in the bottom surface of the channel passageway, in that the wire guide is to be positioned within the channel, and in that the slidable member surface extends into the channel to contact the wire guide. The handle is further characterized in that the bottom surface of the channel is coplanar to the longitudinal axis of the elongated member, in that the axis of the slidable member is inclined relative to the longitudinal axis and in that the slidable member surface is substantially parallel to the bottom surface.

BRIEF DESCRIPTION OF THE DRAWING

FIG. 1 depicts an illustrative lockable wire guide control handle of the present invention for grasping and manipulating a wire guide;

FIG. 2 depicts a partially sectioned side view of the control handle of FIG. 1;

FIG. 3 depicts a top view of the control handle of FIG. 1;

FIG. 5 depicts a partially sectioned view of another embodiment of the invention;

FIG. 6 depicts a partially sectioned view of a further embodiment of the invention;

FIG. 7 depicts a partially cross-sectioned view of the control handle of FIG. 5 taken along the line 7—7;

FIG. 8 depicts a partially cross-sectioned view of the control handle of FIG. 6 taken along the line 8—8; and FIG. 9 depicts an enlarged partial view of another embodiment of the control handle channel of FIG. 8.

DETAILED DESCRIPTION

Figure 4:
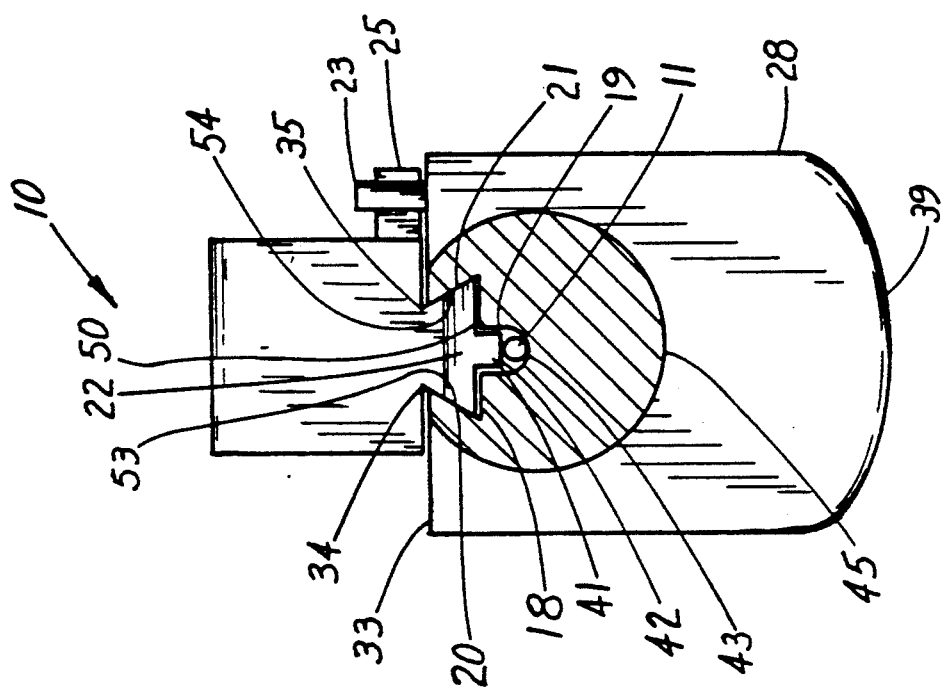
FIG. 4 depicts a cross-sectional view of the control handle of FIG. 3 along the line 4—4.

Depicted in FIG. 1 is an illustrative lockable wire guide control handle 10 for grasping and manipulating wire guide 11. The lockable control handle comprises an elongated member 12 including inclined slot 19 communicating with enclosed passageway 15 for positioning the wire guide therein and thumb slide 13 for locking or fixing the position of the wire guide in the inclined slot. Elongated member 12 includes proximal portion 14 with enclosed passageway 15 extending longitudinally therethrough. Distal portion 16 includes dovetail-shaped retention channel 17 extending longitudinally therethrough with inclined slot 19 extending longitudinally through flat bottom channel surface 18. Inclined slot 19 is angled distally away from the flat bottom channel surface for easy insertion of the wire guide. For further easing the insertion of the wire guide into the inclined slot, the distal end thereof includes internal taper 27. At the proximal end, the inclined slot is angled outwardly away from enclosed passageway 15 for fixedly positioning the wire guide in the slot without kinking the guide. Retention channel 17 also includes angled lateral surfaces 20 and 21 at a standard included angle of 60 degrees to form the well-known dovetail-shaped configuration.

Thumb slide 13 includes a mating dovetail-shaped tenon 22 extending laterally therealong and positioned in retention channel 17 for retaining the thumb slide in the channel. Stop 23 is positioned adjacent channel opening 24 and extends laterally from distal portion 16 for preventing thumb slide 13 from being extended beyond a predetermined forward position and out distal end 36 of the channel. Thumb slide 13 includes side catch 25 extending laterally from flexible member 26 for engaging the stop when the thumb slide is moved to a full forward position. The full forward position of the thumb slide is utilized for front loading wire guide 11 into inclined slot 19 and then enclosed passageway 15. Flexible member 26 flexes into relief channel 52 of the thumb slide for passage of the catch past the stop.

Distal portion 16 of the control handle also includes finger retention projections 28 and 29 extending radially therefrom and positioned longitudinally apart opposite retention channel opening 24. Finger projections 28 and 29 grip the physician's index finger for easily and controllably moving slide 13 with the physician's thumb between the full forward position and partially closed proximal end 30 of the retention channel. The finger retention projections are also utilized by the physician for moving the wire guide longitudinally in a vessel of the patient's vascular system. Proximal portion 14 is cylindrical for easily rotating the handle by the physician.

Depicted in FIG. 2 is a partially sectioned side view of lockable wire guide control handle 10 of FIG. 1 with thumb slide 13 fixedly positioning wire guide 11 in inclined slot 19 of retention channel 17. Depicted in FIG. 3 is a top view of lockable wire guide control handle 10 of FIG. 1, and depicted in FIG. 4 is a cross-sectional view of the lockable wire guide 10 of FIG. 3 along the line 4—4.

Elongated member 12 basically comprises a 0.500"×0.638"×3.250" piece of commercially available LEXAN ™ plastic material injection molded, as shown. Thumb slide 13 comprises a 0.401"×0.367"×0.875" piece of CELCON ™ plastic material also injection molded, as shown. Elongated member 12 is approximately 3.250" in length with a maximum width of 0.500" about shoulders 31 and 32 of respective finger projections 28 and 29 as depicted in FIG. 3. Flat top surface 33 of distal portion 16 is approximately 1.875" in length and has a variable width, as shown, with a maximum width of 0.500" about shoulders 31 and 32. Surface 33 is recessed approximately 0.030" from outer surface 44 of cylindrical proximal portion 14. Channel opening 24 in flat surface 33 is approximately 0.142" in width and 1.813" in length for thumb slide 13 to slide between open distal end 36 and partially closed proximal end 30 of the retention channel.

Retention channel 17 is approximately 0.068" in depth with lateral surfaces 20 and 21 forming a standard 60 degree included angle to form the dovetail shape with flat bottom surface 18. Rounded bottom surface 43 of inclined slot 19 forms an angle of 2.5 degrees with flat bottom surface 18 and extends longitudinally therein to a maximum depth of approximately 0.085" about distal end 36. Internal taper 27 is a 30 degree taper extending into inclined slot 19 for approximately 0.075" from distal end 36. The proximal end of the inclined slot continues through flat bottom channel surface 18 and then into enclosed passageway 15. Inclined slot 19 is approximately 0.052" in width. Positioned on shoulder 31 adjacent channel opening 24 is elliptically shaped stop 23. The approximately 0.045" wide stop extends from flat surface 33 approximately 0.063". The center of the rear semicircular surface of the stop is positioned approximately 0.725" from distal end 36 of the distal portion. The center of the front semicircular surface of the stop is approximately 0.070" forward. The stop is also positioned approximately 0.176" from the longitudinal center of the distal portion.

Distal portion 16 further includes finger retention projections 28 and 29, which are positioned longitudinally approximately, 0.875" apart with projection 28 extending back from distal end 36 approximately 0.625". Finger projections 28 and 29 include 0.250" radius curves 46–49 at the base thereof, which merge with outer cylindrical surface 45 of distal portion 16 having a 0.360" outside diameter. The finger retention projections are rounded at the tip thereof with a 0.312" radius, as shown by curved surface 39 in FIG. 4.

Proximal portion 14 of the elongated member is cylindrical with an outside diameter of 0.320". The proximal portion includes offset enclosed passageway 15 extending longitudinally therethrough and having a central longitudinal axis approximately 0.075" from outer cylindrical surface 44, as shown in FIG. 2. Enclosed passageway 15 is offset from the center of the cylindrical proximal portion as well as inclined slot 19 for easily positioning the wire guide therethrough and torquing the fixedly positioned wire guide when in a patient's blood vessel. Enclosed passageway 15 has a diameter of approximately 0.071" with internal taper 37 forming an included angle of 60 degrees with an outside diameter of 0.120" about proximal end 38 of the proximal portion.

Thumb slide 13 is approximately 0.875" long, 0.300" high, and 0.286" wide with catch 25 extending approximately 0.081" laterally therefrom. Positioned about a proximal corner of the thumb slide is flexible member 26, which extends proximally approximately 0.375" in length. The flexible member is approximately 0.050" thick and has a height of 0.135" at the proximal end of the thumb slide. Positioned next to flexible member 26 is a 0.375" long by 0.075" wide relief channel 52, which allows for the lateral movement of the flexible member.

The proximal end of the thumb slide includes top curved thumb contact surface 51 having a radius of approximately 0.625". Top distal end curved surface 40 of the thumb slide has a radius of approximately 0.188" for comfortable thumb slide movement by the physician. The thumb slide is pushed on elbows 34 and 35 sliding on flat top surface 33 to the full forward position to insert a wire guide into the inclined slot and enclosed passageway. When the guide is positioned in the slot and passageway, the thumb slide is pulled back to fixedly position or lock the guide in the inclined slot. The thumb slide extends approximately 0.300" above top surface 33 of the elongated member with dovetail tenon 22 extending 0.068" therefrom and into retention channel 17. Dovetail tenon 22 includes bottom tenon surface 50 and lateral surfaces 53 and 54 forming an included 60 degree angle. Flat bottom surface 50 is approximately 0.188" in width.

Approximately 0.075" from the distal end of the thumb slide, inclined projection 41 extends farmost for approximately 0.033". Inclined projection 41 includes inclined bottom surface 42 which forms a 2.5 degree angle with respect to flat bottom tenon surface 50. The proximal and distal bottom ends of the thumb slide are chamfered at a 45 degree angle for approximately 0.050" and 0.075" respectively, as shown. Inclined projection 41 extends from bottom surface 50 of the dovetail tenon and has a width of approximately 0.032" for insertion into inclined slot 19. Inclined surface 42 is substantially parallel to bottom surface 43 of the inclined slot. The parallel relationship of these two inclined surfaces allows for a variable, uniform width spacing between the inclined projection and slot for accepting a variety of wire guide diameters. The parallel relationship of the inclined slot and projection also maximizes the contact surface area for grasping the wire guide without kinking or bending it.

Various alternative materials may be utilized to form the elongated member and thumb slide of the control handles. The control handles may alternatively be machined or formed utilizing other well-known techniques other than injection molding. It is further contemplated that the shape of the mating retention channel and tenon may also be modified to something other than a dovetail configuration. The stop and catch may also be repositioned, but not to the ends of the inclined slot or enclosed passageway, which will deter easy loading of the wire guide. In summary, the offset enclosed passageway of the cylindrical proximal portion of the handle provides for rotation of a wire guide contained therein. In addition, the thumb slide, normally pulled back to fixedly position the wire guide in the inclined slot, may be utilized in combination with the finger retention projections to control longitudinal movements of the guide with a patient's vessel. The thumb slide may be also utilized to release and grasp the wire guide for feeding the wire guide into the patient's vessel. The handle is pulled back to remove the locked wire guide from the vessel.

In the preceding embodiments, passageway 15 is enclosed and communicates with retention channel 17 and inclined slot 19 in which thumb slide 13 operates.

In the embodiments of FIGS. 5 and 6, like references designate like parts in the other embodiments. Passageway 15 and channel 17 extend along the member 12 without an inclined slot or section. In all embodiments, the slidable member operates on a single planar wire guide surface, whether it is the inclined surface or the single coplanar passageway and channel surface of FIGS. 5 and 6. In all of the embodiments, the base of the slidable member is parallel to the base of the respective passageway or channel throughout the length of the passageway or channel in which the slidable member operates.

In the preceding embodiments, the retention channel has a dovetail-shaped mortise and the same form of arrangement can be employed in the embodiments of FIGS. 5 and 6. The latter illustrates an alternative form of retention arrangement, and it is to be understood that that arrangement could alternatively be employed in the preceding embodiments.

The handles of FIGS. 5 and 6 each comprise a passageway 15 and channel 17 which are coplanar and extend longitudinally throughout member 12. In distal portion 16 or near the distal end in FIG. 5, the slidable member 61 is slidably mounted for movement along an axis 62 inclined with respect to the lower surface of wire guide support surface 67. The axis 62 is formed by a slot in a plate 63 on one side of member 61 and a corresponding slot in another plate on the other side of the member 61. The plates can form side walls of member 12 if required. Two rods 64,65 positioned in or through member 61 engage in the slots and guide the member 61 along the inclined axis. It will be appreciated that as the member 61 is moved along the inclined axis in either direction thereof, the bottom surface 66 will remain parallel to wire guide support surface 67 of channel 17.

The member 61 is moved into a locking condition with respect to the wire guide by moving the member in a direction towards proximal portion 14 or the proximal end of the handle. When bottom surface 66 firmly engages the wire guide, the latter is locked to the handle.

The member 61 is moved into an unlocked condition by moving in a direction towards distal portion 16 or the distal end of the handle. Bottom surface 66 moves away from the wire guide but still maintains the parallel relationship, whereby the wire guide can be moved along the handle to another position or a new wire guide can be longitudinally inserted into the handle without member 61 obstructing that process in any way.

Depicted in FIG. 7 is a partially cross-sectioned view of control handle 10 of FIG. 5 taken along the line 7—7. Slide 61 is positioned in channel 17 and slidably moveable via rods 64 and 65 laterally positioned through the slide and into slots 56 and 62 in respective channel walls 57 and 63. Projection 68 extends from the bottom of the thumb slide and into slot 55, which has a bottom surface 67 that is coplanar with bottom surface 58 of passageway 15. As thumb slide 61 is moved longitudinally in channel 17, bottom surface 69 of slide 61 as well as bottom surface 66 of projection 68 remain parallel to bottom channel surface 76 and wire guide support surface 67, respectively. The spacing between these surfaces varies as the slide is longitudinally moved in the channel; however, the surfaces remain parallel at all positions of the slide in the channel.

In the embodiment of FIG. 6 the slidable member 71 is mounted in a manner similar to that of member 61. One, 72, of two plates or sides of member 12 is shown with an axial slot 73 inclined with respect to the wire guide support surface 78. Rods 74 and 75 extending from the sides of member 71 engage in the lateral slot 73 and guide the member 71 along the inclined axis. The lower surface 77 of the member 71 remains parallel to wire guide support surface 78, and thus the wire guide, at all positions of the member 71 along the axis 73.

In the FIG. 6 embodiment, the member 71 is moved towards the distal end of the handle to lock the wire guide, and is moved towards the proximal end of the handle in order to release the wire guide.

Depicted in FIG. 8 is a partially cross-sectioned view of control handle 10 of FIG. 6 taken along the line 8—8. Slide 71 is positioned in channel 17 with laterally extending rods 74 and 75 positioned in slots 59 and 73 in respective channel walls 60 and 72 laterally positioned on opposite sides of the channel. Bottom surface 77 of the slide remains substantially parallel to bottom wire guide support surface 78. The spacing between surfaces 77 and 78 is variable as the slide is moved longitudinally within the channel; however, the surfaces remain substantially parallel in all positions of the slide within the channel.

Depicted in FIG. 9 is an enlarged, partial view of another embodiment of bottom channel surface 78 of the control handle of FIG. 8. The bottom surface includes a V-shaped slot 70 for the positioning of a wire guide therein. This V-shaped slot minimizes the lateral movement of the wire guide when positioned therein.

In FIGS. 5 and 6 the members 61 and 71 are shown to have inclined upper surfaces. Clearly, the upper parts of these members can be any shape, such as rounded or square shaped. The axes 62 and 73 should, however, be inclined.

It is to be understood that the above-described wire guide control handle is merely an illustrative embodiment of the principles of this invention and that other embodiments may be devised by those skilled in the art without departing from the spirit and scope of this invention. It is contemplated that various other materials may be utilized to form the elongated member and thumb slide of the control handle. The control handle may alternatively be machined or formed utilizing other well-known techniques other than injection molding as indicated with the preferred embodiment. It is further contemplated that the shape of the mating retention channel and tenon may also be modified to something other than a dovetail configuration. The stop and catch may also be repositioned, but not to the ends of the inclined slot or enclosed passageway, which will deter easy loading of the wire guide. In summary, the offset enclosed passageway of the cylindrical proximal portion of the handle provides for rotation of a wire guide contained therein. In addition, the thumb slide normally pulled back to fixedly position the wire guide in the inclined slot may be utilized in combination with the finger retention projections to control longitudinal movement of the guide within a patient's vessel. The thumb slide may be also utilized to release and grasp the wire guide for feeding the wire guide into the patient's vessel. The handle is pulled back to remove the locked wire guide from the vessel.

What is claimed is:

1. A wire guide control handle comprising:
an elongated member having an enclosed passageway extending longitudinally therein and a channel communicating with said enclosed passageway for receiving a wire guide, said channel including a support surface for supporting said wire guide; and
a slide positioned and slidable in said channel and having a bottom surface for engaging and fixedly positioning said wire guide in said channel, said slide having a plurality of positions in said channel and being slidable in said channel such that said bottom surface of said slide and said support surface of said channel are substantially parallel to one another and variably spaced from one another at all of said positions of said slide in said channel.

2. The handle of claim 1 wherein said support surface of said channel includes a slot therein and extending longitudinally therethrough.

3. The handle of claim 2 wherein said slot is V-shaped.

4. The handle of claim 2 wherein said slide includes a projection extending therefrom and into said slot, said slot and said projection each having a surface such that said surface of said slot and said surface of said slide are substantially parallel to one another and variably spaced form one another at all of said positions of said slide in channel.

5. The handle of claim 1 wherein said channel has a lateral surface with a slot therein inclined to said support surface of said channel.

6. A wire guide control handle comprising:
an elongated member having a passageway extending longitudinally therein for receiving a wire guide, a proximal portion of said passageway being enclosed, a distal portion of said passageway including a channel for receipt and retention of a slide, said channel including a support surface for supporting said wire guide; and
a slide positioned and slidable in said channel and having a bottom surface for engaging and fixedly positioning said wire guide in said channel, said slide having a plurality of positions in said channel and being slidable in said channel such that said bottom surface of said slide and said support surface of said channel are substantially parallel to one another and variably spaced form one another at all of said positions of said slide in said channel.

7. The handle of claim 6 wherein said bottom surface of said channel includes a slot therein and extending longitudinally therethrough.

8. The handle of claim 7 wherein said slot is V-shaped.

9. The handle of claim 6 wherein said channel has a lateral surface with a slot therein inclined to said bottom surface of said channel.

10. A wire guide control handle comprising an elongated member (12) having a passageway (15) for the support and passage therethrough of a wire guide (11) and wire guide channel means (19) in communication with the passageway and also serving to support the wire guide therein, said handle also comprising a slidable member (13) having a surface (42) thereof slidably movable in a channel (19) of said channel means (19) and serving to engage with or disengage from the wire guide when in the channel in order to lock or release the guide in said channel means (19), and means (17,22) for causing the slidable member to slide along an axis inclined to a wire guide support surface (43,67) of said channel means (19), characterized in that said slidable member surface (42) extends only over one planar wire guide support surface and is substantially parallel to said wire guide support surface (43,67) during all of the movement of the slidable member and that the passageway (15) is enclosed about a proximal portion thereof, and in that a distal portion of the passageway is channelled to receive and retain the slidable member, and to receive and position the wire guide on the wire guide support surface (43,67).

11. A handle according to claim 10, characterized in that the bottom surface of said channel is inclined relative to the longitudinal axis of the elongated member, in that the axis of the slidable member is parallel to the said longitudinal axis, and in that the said slidable member surface (42) is inclined at substantially the same angle of inclination relative to the longitudinal axis as the said bottom surface (43).

12. A handle according to claim 10, characterized int hat the bottom surface of said channel is coplanar to the longitudinal axis of the elongated member, in that the axis (62) of movement of the slidable member is inclined relative to said longitudinal axis, and in that said slidable member surface (66) is substantially parallel to the said bottom surface (67).

13. A handle according to claim 10, characterized in that a slot is formed in a bottom surface of the channelled passageway, in that the wire guide is to be positioned within said channel, and in that said slidable member surface extends into said channel (19) to contact the wire guide.

14. A handle according to claim 13, characterized in that the bottom surface of said channel is inclined relative to the longitudinal axis of the elongated member, in that the axis of the slidable member is parallel to said longitudinal axis, and in that said slidable member surface (42) is inclined at substantially the same angle of inclination relative to the longitudinal axis as the said bottom surface (43).

15. A handle according to claim 13, characterized in that the bottom surface of said channel is coplanar to the longitudinal axis of the elongated member, in that the axis (62) of movement of the slidable member is inclined relative to the said longitudinal axis, and in that the said slidable member surface (66) is substantially parallel to the said bottom surface (67).

16. A handle according to claim 10, characterized in that the slidable member is retained within the channel support means by a dovetail tenon (22) and mortise arrangement (20,21).

17. A handle according to claim 10, further characterized by a stop (23) and catch (25) arrangement for retention of the slidable member.

18. A handle according to claim 13, characterized in that said passageway is offset relative to the inclined slot.

19. A handle according to claim 10, characterized in that the proximal end of the enclosed passageway includes an internal taper for receiving the wire guide.

* * * * *